(12) United States Patent
Parmentier et al.

(10) Patent No.: US 8,187,646 B2
(45) Date of Patent: May 29, 2012

(54) NUCLEOTIDE PYROPHOSPHATASE INHIBITOR AND COENZYME REGENERATING SYSTEMS

(75) Inventors: Sofie Parmentier, Vichte (BE); Eric Vandamme, Ghent (BE); Joeri Beauprez, Bredene (BE); Filip Arnaut, Roosdaal (BE)

(73) Assignee: Puratos N.V., Groot-Bijgaarden (BE)

( * ) Notice: Subject to any disclaimer, the term of this patent is extended or adjusted under 35 U.S.C. 154(b) by 869 days.

(21) Appl. No.: 11/570,923

(22) PCT Filed: Jun. 29, 2005

(86) PCT No.: PCT/BE2005/000104
§ 371 (c)(1),
(2), (4) Date: Sep. 12, 2008

(87) PCT Pub. No.: WO2006/000066
PCT Pub. Date: Jan. 5, 2006

(65) Prior Publication Data
US 2010/0028493 A1   Feb. 4, 2010

(30) Foreign Application Priority Data
Jun. 29, 2004 (EP) .................... 04447155

(51) Int. Cl.
*A21D 10/00* (2006.01)
(52) U.S. Cl. ........... 426/61; 426/331; 426/549; 435/195
(58) Field of Classification Search .................. 426/61, 426/331, 549; 435/195
See application file for complete search history.

(56) References Cited

U.S. PATENT DOCUMENTS

| 3,561,974 A | | 2/1971 | Hansen | |
| 5,451,417 A | * | 9/1995 | Freyn et al. | 426/551 |
| 6,291,005 B1 | | 9/2001 | Fuchs et al. | |
| 6,306,445 B1 | * | 10/2001 | Xu et al. | 426/20 |

FOREIGN PATENT DOCUMENTS

| JP | 56-051946 | 5/1981 |
| JP | 57-146574 | 9/1982 |
| JP | 04-346745 | 12/1992 |
| RU | 2 158 513 | 11/2000 |
| WO | WO 2004/007706 | 1/2004 |
| WO | WO 2004/037003 | 5/2004 |

* cited by examiner

*Primary Examiner* — D. Lawrence Tarazano
*Assistant Examiner* — Hamid R Badr
(74) *Attorney, Agent, or Firm* — Knobbe Martens Olson & Bear LLP

(57) ABSTRACT

The present invention is related to a method for inhibiting nicotinamide coenzyme degradation in a cereal flour or wheat based product, comprising the addition of an effective amount of nucleotide pyrophosphatase inhibitor to said cereal flour based product, product such as a wheat based product. A further aspect of the present invention is a nucleotide pyrophosphatase having an amino acid N-terminal sequence being (G)IDDRHEVDLPPRP. In another aspect of the present invention, a dough comprising a nucleotide pyrophosphatase inhibitor such as pyrophosphate, and optionally a coenzyme regeneration system comprising at least one NAD(P) or NAD(P)H dependent hydrogenase or dehydrogenase is disclosed. Preferably the coenzyme regeneration system comprises (consists of) mannitol dehydrogenase and D-fructose.

13 Claims, 3 Drawing Sheets

($\blacksquare$ NAD$^+$; $\square$ NADH)

($\blacksquare$ NAD$^+$; $\square$ NADH)

SEQUENCE LISTING

<160> NUMBER OF SEQ ID NOS: 2

<210> SEQ ID NO 1
<211> LENGTH: 14
<212> TYPE: PRT
<213> ORGANISM: Triticum durum

<400> SEQUENCE: 1

Gly Ile Asp Asp Arg His Glu Val Asp Leu Pro Pro Arg Pro
1               5                   10

<210> SEQ ID NO 2
<211> LENGTH: 13
<212> TYPE: PRT
<213> ORGANISM: Triticum durum

<400> SEQUENCE: 2

Ile Asp Asp Arg His Glu Val Asp Leu Pro Pro Arg Pro
1               5                   10

NUCLEOTIDE PYROPHOSPHATASE INHIBITOR AND COENZYME REGENERATING SYSTEMS

FIELD OF THE INVENTION

The present invention is related to the use of natural electron transfer agents present in cereal flour or wheat based products such as dough systems.

STATE OF THE ART

The use of oxidising and reducing agents as bread improvers is well known. Oxidants exert their positive effect by the oxidising action of sulphydryl groups in the gluten network, resulting in stronger dough. Reducing agents, on the other hand, such as cysteine or reduced glutathione, will generally result in weaker doughs.

Chemical agents, e.g. bromate, iodate and azodicarbonamide (ADA), were used in the past. However there is a great interest to replace these chemical oxidising agents by biological oxido-reductants, like L-threo ascorbic acid (vitamin C). This is now the most widely used oxidising agent. There is also an interest in oxidising enzymes, such as lipoxygenase, peroxidase and glucose oxidase, for their positive effect on baking quality. Natural electron transfer biological oxidoreductants, such as nicotinamide adenine dinucleotide ($NAD^+$), and its phosphate ($NADP^+$), flavin adenosine nucleotide (FAD), flavin mononucleotide (FMN), the ubiquinones, the cytochromes etc. have been considered to improve the quality of yeast raised baked goods (Tomlinson, J. D., Robertson, J. A. & Thomson, W. K. (1988). Novel improvers for flour and yeast raised baked goods; WO8803365). Moreover it is reported that $NAD(P)^+$-dependent and $NAD(P)^+$-independent dehydrogenases can be used as bread improvers (Xu & Wagner, 1999; Methods for using dehydrogenases in bread; WO9957986). The thioredoxin system can also improve the quality of bread and baked goods, by the reduction of glutenins and gliadins; this system is however dependent on the presence of NADPH (Buchanan & Kobrehel, 1998; Use of thiol redox proteins for reducing protein intramolecular disulfide bonds, for improving the quality of cereal products, dough and baked goods; EP0863154.)

AIMS OF THE INVENTION

The present invention aims to provide an enhanced use of natural electron transfer agents present in cereal flour or wheat based products such as dough systems (doughs). More in particular, the present invention aims to improve the action of nicotinamide coenzymes in dough and baking quality.

SUMMARY OF THE INVENTION

The present invention concerns a method for inhibiting nicotinamide coenzyme degradation in a cereal flour based product, such as a wheat based product, comprising the addition of nucleotide pyrophosphatase (NPP) inhibitor(s) to said cereal flour based product, such as a wheat based product. In particular, the present invention concerns a method for inhibiting nicotinamide coenzyme degradation in a cereal flour based product, such as a wheat based product, comprising the addition of an effective amount of nucleotide pyrophosphatase inhibitor(s) to said cereal flour based product, such as a wheat based product.

Advantageously, at least one (one or more) NPP inhibitor(s) is added to the cereal flour based product, such as a wheat based product.

By an "effective amount" of NPP inhibitor is meant an amount of inhibitor that results in the inhibition (partial or complete) of nicotinamide coenzyme degradation by said NPP. In general the inhibitor is added in an amount of about 0.1-3%, preferably of about 0.2-2.5%, more preferably of about 0.5-1% on flour weight.

Preferably at least a 50%, 60%, more preferably at least a 70%, 80%, 90% and most preferably a complete to nearly complete inhibition of the NPP in the cereal flour based product, such as a wheat based product, is obtained by the addition of said inhibitor.

Advantageously, the inhibitor is added to a cereal flour based product, such as a wheat based product, to which a (de)hydrogenase, more in particular a NAD(P) or NAD(P)H dependent hydrogenase or dehydrogenase has been added. This hydrogenase or dehydrogenase advantageously is a native (de)hydrogenase, or a (de)hydrogenase naturally present in the cereal flour based product, such as a wheat based product.

Preferably, the nucleotide pyrophosphatase inhibitor is pyrophosphate, (e.g. sodium or calcium pyrophosphate) but other inhibitors such as thiol-based inhibitors can also be used. EDTA, reduced glutathione and L-cysteine are examples of thiol-based food grade inhibitors. Also ADP (about 1-2 mM e.g), tripolyphosphate and metaphosphate are able to inhibit said NPP in wheat flour.

In an embodiment according to the invention, pyrophosphate is added to the cereal flour or wheat based product, possibly in combination with one or more other NPP inhibitors ("other" standing for other than a pyrophosphate such as calcium or sodium pyrophosphate). Calcium and sodium pyrophosphate are preferably added at about 10-150 mM, preferably at about 20-120 mM, more preferably at about 50-100 mM. A preferred concentration of (calcium) pyrophosphate is 0.2-2.5%, more preferably 0.5-1% on flour weight.

L-cysteine and DTT (dithiothreitol) are preferably added at about 2-6 mM, ADP at about 0.5-2 mM. Reduced glutathione preferably is used at 2-20 mM, most preferably at about 10 mM. EDTA preferably is used at 1-20 mM. From a concentration of 4 mM EDTA on, complete inhibition of the wheat flour NPP was observed (in vitro). A pre-incubation period of about 1 hour may be advantageous for some of the inhibitors.

A "cereal flour based product" as used herein refers to a dough prepared from a cereal (grain) flour. A "wheat based product" as used herein refers to a dough prepared from wheat flour. The term "dough" or "dough system" refers to a composition comprising (wheat) flour and a liquid (e.g. water). The dough may further comprise other typical dough ingredients such as e.g. yeast and/or chemical leavening means. The dough may be a chemically-leavened (wheat) dough or a yeast-raised (wheat) dough. In a preferred embodiment, the wheat based product is a yeast-raised dough, preferably a yeast-raised wheat dough.

In a preferred embodiment, the method of the present invention further comprises adding a coenzyme regeneration system to the cereal flour based product, such as a wheat based product. A "coenzyme regeneration system" or "coenzyme regenerating system" as used herein refers to a composition comprising (consisting of) one or more enzymes effective in regenerating $NAD^+$ from NADH and vice versa. The coenzyme regeneration system preferably comprises (consists of) at least one (one or more) NAD(P) or NAD(P)H dependent hydrogenase or dehydrogenase. A preferred dehydrogenase is mannitol dehydrogenase (MDH). Advantageously said MDH is added together with fructose (e.g. D-fructose). In an embodiment according to the invention about 50-1000 U MDH, more preferably about 100-500 U MDH obtained from e.g. *Leuconostoc pseudomesenteroides* is added per 100 g flour together with about 0.5-1.5 g fructose, more preferably about 1 g fructose.

Depending on which (natural) enzymes are already present in the dough, a hydrogenase, a dehydrogenase, or both a hydrogenase and a dehydrogenase are advantageously added to the cereal flour based product, in particular a wheat based product such as a (wheat) dough. A NADH oxidase in wheat flour can e.g. form $NAD^+$ from NADH. A wheat flour alcohol dehydrogenase, using ethanol (a reaction product of e.g. yeast fermentation) as substrate, can form NADH from $NAD^+$.

In an embodiment according to the invention, enzymes for respectively the reduction and the oxidation of the nicotinamide coenzymes are both added, to ensure proper enzyme circulation (NADH↔$NAD^+$). A formate dehydrogenase (FDH) regeneration system (about 25-75 U FDH from *Candida boidinii* (EC 1.2.1.2)+about 0.2-0.6 g Na-formate e.g. per 100 g flour) proved very useful for the formation of NADH from $NAD^+$. MDH is the preferred enzyme to regenerate $NAD^+$ from NADH.

Said nucleotide pyrophosphatase inhibitor preferably inhibits a nucleotide pyrophosphatase present in the cereal flour based product, more in particular the wheat based product and having an amino acid N-terminal sequence being (G) IDDRHEVDLPPRP (SEQ ID NO: 1) (that is being GID-DRHEVDLPPRP (SEQ ID NO: 1) or IDDRHEVDLPPRP (SEQ ID NO: 2)).

Another aspect of the present invention concerns a nucleotide pyrophosphatase having an amino acid N-terminal sequence being (G) IDDRHEVDLPPRP (SEQ ID NO: 1).

In another aspect of the present invention, a dough comprising a nucleotide pyrophosphatase inhibitor such as pyrophosphate, and optionally a coenzyme regeneration system is disclosed. The coenzyme regeneration system preferably comprises mannitol dehydrogenase and D-fructose, and/or NAD(P) or NAD(P)H dependent hydrogenase or dehydrogenase. The coenzyme regeneration system preferably comprises (consists of) at least one NAD(P) or NAD(P)H dependent hydrogenase or dehydrogenase. A preferred dehydrogenase is mannitol dehydrogenase that advantageously is added together with (D-)fructose.

*Leuconostoc pseudomesenteroides* mannitol dehydrogenase, *Gluconobacter oxydans* mannitol and sorbitol dehydrogenase, and *Candida tenuis* xylose reductase are preferred over some commercial enzymes like the *Thermus flavus* malate dehydrogenase, the *Saccharomyces cerevisiae* alcohol dehydrogenase and the *Leuconostoc mesenteroides* glucose-6-phosphate dehydrogenase.

SHORT DESCRIPTION OF THE DRAWINGS

Figure 5:
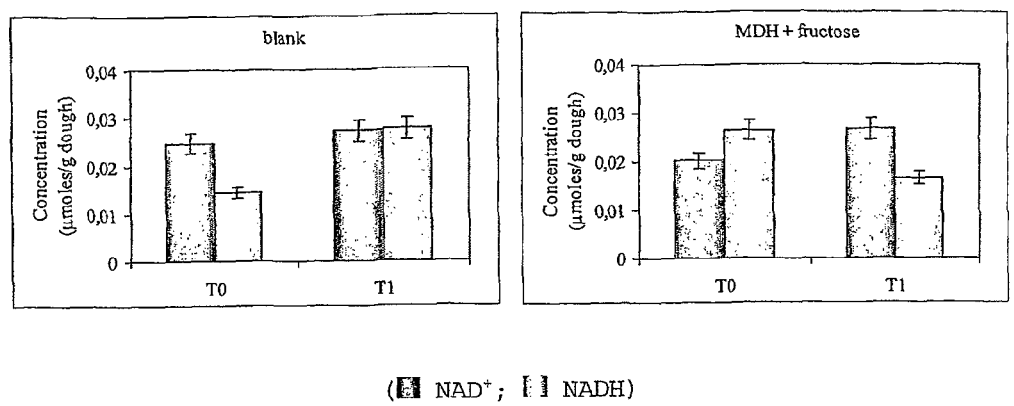

FIG. 5 draws the effect of mannitol dehydrogenase regenerating system on coenzyme concentrations.

Figure 6:
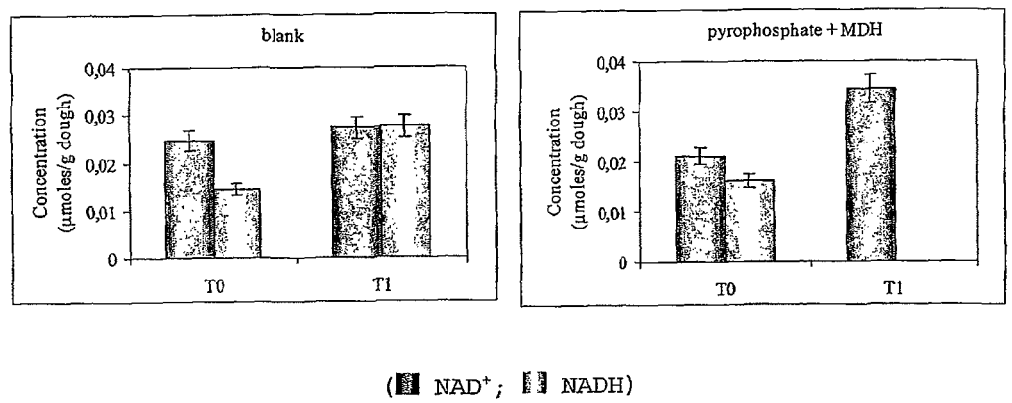

FIG. 6 depicts the combined effect of pyrophosphate and mannitol dehydrogenase on coenzyme concentrations.

DETAILED DESCRIPTION OF THE INVENTION

The present invention exploits the capacity of natural electron transfer agents present in dough systems. More in particular, the nicotinamide coenzymes, NAD(H), are of importance for dough and baking quality. Two aspects have to be considered. First aspect is the inhibition of coenzyme degradation, which takes place in wheat flour. Secondly, a coenzyme regenerating system can be applied to prevent the accumulation of coenzymes in either the oxidised or reduced form. A combination of both approaches can also be considered.

An enzyme was found in wheat flour, which is responsible for the degradation of the nicotinamide coenzymes NAD(H). On the basis of the degradation products, NMN (nicotinamide mononucleotide) and AMP (adenosine monophosphates), the enzyme was identified as a nucleotide pyrophosphatase (NPP). The NPP enzyme present in wheat flour was partially purified from a wheat flour extract (see Example 12) by applying a heat treatment (10', 70° C.), an ammonium sulfate precipitation (60% saturation, 0° C.) and an overnight dialysis (0.1 M Tris-HCl, pH 8.5). From a zymogram of a native gel electrophoresis (PAGE) the molecular weight of the NPP present in wheat flour was determined to be about 100-104 kDA. The N-terminal sequence was found to be (G)ID-DRHEVDLPPRP (SEQ ID NOs: 1 and 2).

The nucleotide pyrophosphatase (NPP) present in wheat flour maintains (all or substantially all of) its NPP activity after an incubation of 10 minutes at 70° C. A heat treatment of 10 minutes at 80° C. is necessary to inactivate the enzyme. The pH optimum for $NAD^+$ degradation is situated around pH 9.5-10.5.

This enzyme was not reported in wheat flour before. This enzyme is considered to be negative for bread making quality, since it hampers the natural oxidation-reduction potential of dough. Therefore it is of interest to inhibit this nucleotide pyrophosphatase (NPP). Pyrophosphate was selected as nucleotide pyrophosphatase inhibitor, but also other inhibiting compounds can be considered such as EDTA, L-cysteine, DTT (dithiothreitol) and ADP for instance. L-cysteine and DTT at 4 mM inhibited the NPP at some extent (in vitro tests). ADP in a concentration of 1 mM is able to inhibit the NPP partially. EDTA preferably is used at 1-20 mM. From a concentration of 4 mM EDTA on, complete inhibition of the wheat flour NPP could be observed. Upon addition of divalent ions like $Mg^{+2}$ and $Mn^{+2}$, the enzyme could however be reactivated partially when inhibited by EDTA. This is not the case for pyrophosphate inhibition. More details on compounds and concentrations tested are given in Example 11.

Example 1

In Vitro Inhibition of Nucleotide Pyrophosphatase by Pyrophosphate

Figure 1:
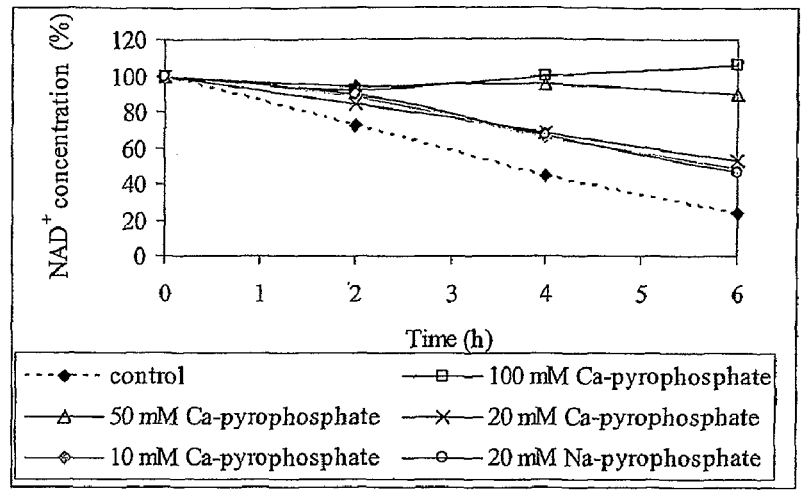
FIG. 1 represents in vitro inhibition of wheat flour nucleotide pyrophosphatase at different pyrophosphate concentrations.

As an example of nucleotide pyrophosphatase inhibition, pyrophosphate was tested. The wheat flour nucleotide pyrophosphatase enzyme could be inhibited by the addition of pyrophosphate (FIG. 1). A concentration of 50 to 100 mM Ca-pyrophosphate ($CaH_2P_2O_7$) could completely inhibit the $NAD^+$ degradation by a wheat flour extract. Partial inhibition could be obtained with 20 and 10 mM pyrophosphate.

An excess of bivalent metal ions ($MgCl_2$, $MnCl_2$, $ZnCl_2$ and $CaCl_2$) could not reactivate the enzyme. Moreover the added pyrophosphate is split into phosphate by the flour extract. This suggests that pyrophosphate is a competitive inhibitor of the wheat flour nucleotide pyrophosphatase.

The NPP enzyme of the invention is also completely inhibited by a 100 mM concentration of sodium pyrophosphate ($Na_2H_2P_2O_7$).

More details on the in vitro NPP inhibition testing are given in Example 11.

Example 2

Dough Systems with Pyrophosphate

Figure 2:
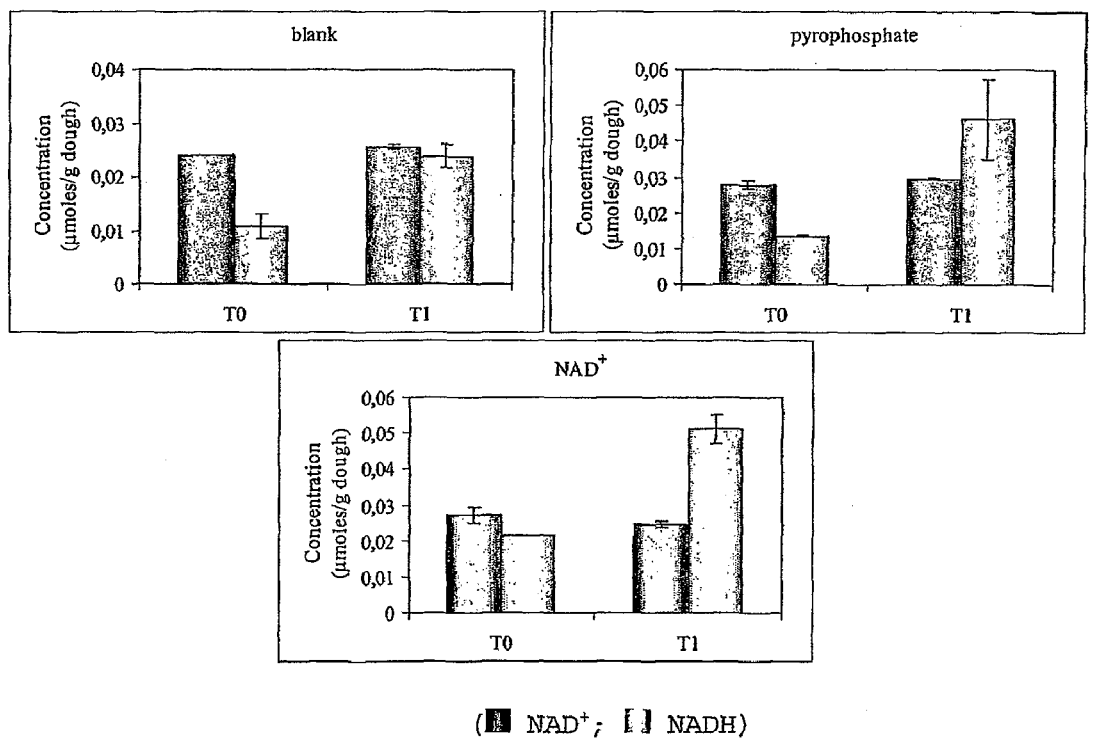
FIG. 2 represents the effect of $NAD^+$ and pyrophosphate on coenzyme concentrations.

In vitro experiments (see Examples 1 and 11) revealed that pyrophosphate is a good inhibitor of the wheat flour nucleotide pyrophosphatase. The effect of pyrophosphate on coenzyme degradation in dough systems was also tested (FIG. 2). Both the oxidised form ($NAD^+$) and the reduced form (NADH) were determined before (T0) and after (T1) 60 minutes of dough resting at 25° C. On the addition of pyrophosphate (e.g. 0.3 g calcium pyrophosphate per 100 g flour), higher coenzyme concentrations were observed. The coenzyme profile was comparable to the profile when $NAD^+$ (e.g. 0.005 g $NAD^+$ per 100 g flour) was added to the dough systems. This supports the hypothesis that pyrophosphate is able to reduce coenzyme degradation taking place in dough systems.

More details on coenzyme extraction and measurement methods are given in Examples 7-8. Details on the in pano test system with mini doughs are given in example 9.

Example 3

Coenzyme Regenerating System

Figure 3:
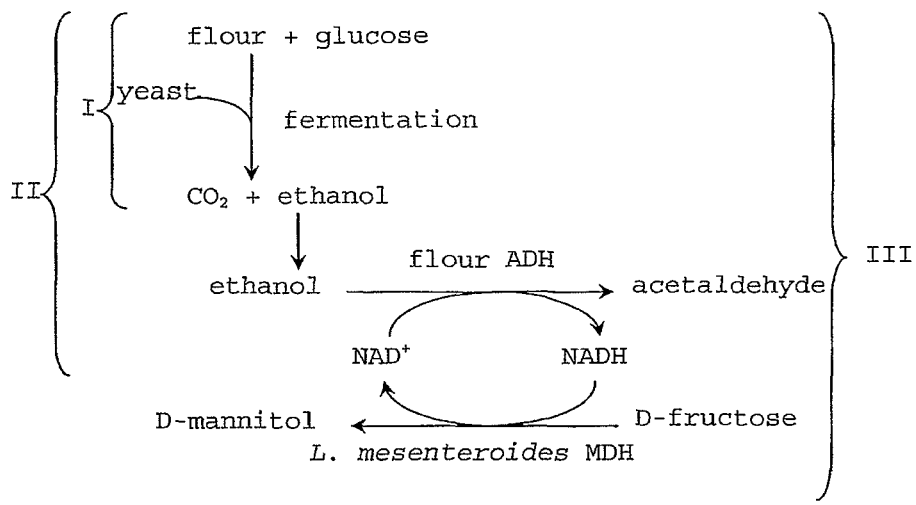
FIG. 3 depicts the principle of the alcohol dehydrogenase/mannitol dehydrogenase coupled enzyme system.

In dough systems, coenzyme conversions take place. Coenzyme reduction is the result of a series of reactions (FIG. 3). During the dough resting period, yeast is fermenting the sugars, present in flour and resulting from enzymatic starch breakdown, into ethanol (I). Ethanol is a substrate for the flour alcohol dehydrogenase, which will reduce $NAD^+$ into NADH (II). NADH can however be reoxidised by the use of a NAD(P)$^+$-dependent dehydrogenase. For this purpose, the *Leuconostoc pseudomesenteroides* mannitol dehydrogenase (MDH) can be selected. This enzyme oxidises NADH into $NAD^+$ with the simultaneous reduction of D-fructose to D-mannitol (III).

A crude *L. pseudomesenteroides* enzyme extract (sonication in a 0.05 M acetate buffer (pH 6.0), centrifugation (10000 rpm, 15 min., GSA rotor) can be used. Alternatively, this crude extract may be further purified by an ammonium sulfate precipitation step (60% saturation, 0° C.), followed by centrifugation (7000 rpm, 15 min., GSA rotor), and overnight dialysis against a 0.05 M acetate buffer (pH 6.0). This dialysed fraction was used as a purified enzyme extract.

*L. pseudomesenteroides* and especially *L. pseudomesenteroides* strains ATCC 12291 and B-512F were found very suitable sources of MDH. MDH may be obtained from other sources.

When *Gluconobacter oxydans* was used as enzyme source (MDH, SDH), a crude enzyme extract was prepared by sonication of *Gluconobacter* cells in 0.1M potassium phosphate buffer (pH 6.0) and the cell debris removed by centrifugation (1000 rpm, 15 min, GSA rotor).

Example 4

In Vitro Coenzyme Regenerating System

Figure 4:
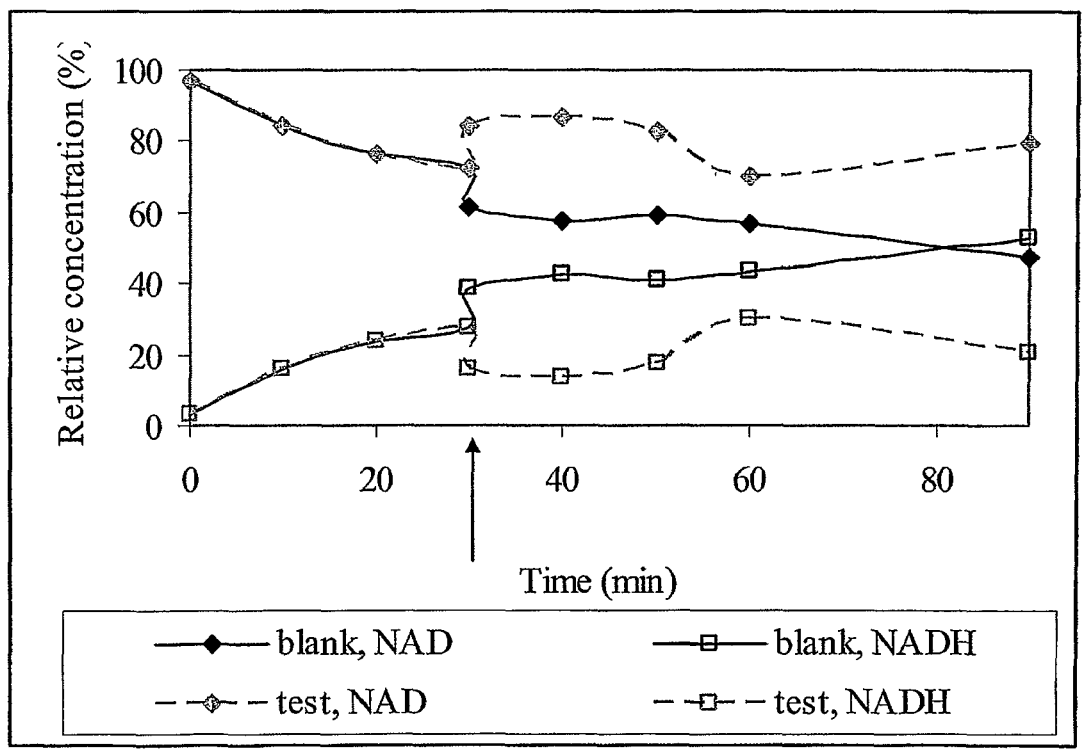
FIG. 4 shows the mannitol dehydrogenase regenerating system after a pre-fermentation (20 min) and a pre-incubation (30 min) period (♦ $NAD^+$; ☐ NADH) (the arrow indicates the addition of MDH and D-fructose).

The coenzyme regenerating principle was tested in vitro with the *L. pseudomesenteroides* MDH (FIG. 4). During the incubation of $NAD^+$ in the presence of wheat flour and yeast, $NAD^+$ is reduced to NADH. When no coenzyme regeneration system is added (blank), $NAD^+$ is further converted to NADH. When the mannitol dehydrogenase system (mannitol dehydrogenase and fructose) is added (test), the formed NADH is regenerated to $NAD^+$. More details on the in vitro MDH regeneration system are given in Example 10.

Example 5

Coenzyme Regenerating System in Dough Systems

The mannitol dehydrogenase regenerating system was tested in dough systems (FIG. 5). In the blank, the NADH concentration increased upon dough resting (the hypothesis for NADH accumulation is explained in the in vitro experiments). When a mannitol dehydrogenase extract was added, together with fructose, no increase in NADH concentration was detected. The NADH concentration decreased, while the $NAD^+$ concentration increased. This indicates that the mannitol dehydrogenase is effective in $NAD^+$ regeneration from NADH. The addition of MDH and fructose resulted in an increase in bread volume.

Besides the mannitol dehydrogenase system, other coenzyme regenerating enzymes (NAD(P) (H)-dependent dehydrogenases) known in the art can also be considered, like *Gluconobacter oxydans* (e.g. LMG 1489) mannitol (MDH) and sorbitol dehydrogenases (SDH), *Candida tenuis* (e.g. CBS 4435) xylose reductase (XR).

See example 9 for details on the baking tests performed with mini doughs (the dough system of this example) and the concentrations of all compounds used therein.

Example 6

Nucleotide Pyrophosphatase Inhibitor and Coenzyme Regenerating System

It is believed that coenzyme degradation affects the coenzyme regenerating system negatively. Therefore a coenzyme regenerating system can be combined with a nucleotide pyrophosphatase inhibitor. As an example pyrophosphate was combined with the mannitol dehydrogenase system described in the previous example.

The combination of pyrophosphate with the mannitol dehydrogenase system, resulted in the significant increase in $NAD^+$ concentration, while NADH disappeared completely (FIG. 6). In this dough the mannitol dehydrogenase is very effective in re-oxidising the NADH formed by the action of the wheat flour dehydrogenase into $NAD^+$.

Example 7

Coenzyme Extraction Method

The oxidised ($NAD^+$) and reduced (NADH) form of the nicotinamide coenzymes were extracted from doughs with an acid and alkaline extraction method respectively. An overview of the methods is given in table 1.

TABLE 1

Acid and alkaline extraction method for the
determination of $NAD^+$ and NADH, respectively

| Acid extraction ($NAD^+$) | Alkaline extraction (NADH) |
| --- | --- |
| Add 2 ml TCA (0.6M) to 1 g of dough | Add 2 ml Tris-acetate (5M, pH 9.5 + 50 mM EDTA) to 1 g of dough |
| Ultra Turrax treatment | Ultra Turrax treatment |
| 30 min., 4° C. (magnetic stirrer) | 30 min., 4° C. (magnetic stirrer) |
| Centrifugation: 15 min, 10000 rpm | Centrifugation: 15 min, 10000 rpm |
| Diethylether extraction (5 times) | |
| Filtration | Filtration |
| HPLC analysis | HPLC analysis |

Example 8

HPLC Method for Coenzyme Determination in Dough

The coenzymes, $NAD^+$ and NADH, can be determined with an isocratic reversed phase HPLC method on a Varian Prostar HPLC system. Separation of the coenzymes $NAD^+$ and NADH was carried out on a Chromsep Microspher 3C18 column (3 μm particle size, 4.6×100 mm, Chrompack). The mobile phase was 96% 0.15 M citrate-sodium phosphate buffer (pH 6.8) containing 1 mM EDTA, and 4% methanol (30° C.). The flow rate was 0.5 ml/min and detection was accomplished by UV absorption at 260 nm (Varian Prostar UV 320).

All samples were filtrated (Sartorius Minisart RC15, 0.45 μm) and sample injection (20 μl) was accomplished with a Varian Prostar 410 autosampler. The nucleotide concentration was measured by the peak area of the chromatogram with calibration curves, which were prepared using a known amount of coenzymes. A complete separation of the four nucleotides ($NAD^+$, $NADP^+$, NADH and NADH) was obtained as such in about 20 minutes.

Example 9

In Pano Test Systems

Baking tests were performed with mini doughs (150 g). The basic composition of the control dough is given in Table 2 below.

TABLE 2

Dough composition for control dough

| | | |
| --- | --- | --- |
| Flour (Surbi) | 100 | g |
| Water (ad) | 58 | g[a] |
| Yeast (Bruggeman) | 5 | g |
| Salt (NaCl) | 2 | g |
| α-amylase (Beldem) (75000 SKB/g) | 1.1 | g[b] |
| Dextrose | 2 | g |

[a]58 g of liquid (water or partially buffer or enzyme solution)
[b]concentration per 100 kg The doughs were kneaded with a pin mixer during 4.5 minutes, after which they were incubated during 20 minutes at 25° C. The dough was sheeted and incubated again at 25° C. during 20 minutes, after which it was sheeted and incubated for 50 minutes at 36° C. and at a relative humidity of 80%. Baking was performed during 20 minutes at an oven temperature of 225° C. Bread volume after baking was determined by the rapeseed displacement method.

The following compounds were tested in mini doughs at the following concentrations (per 100 g flour): Fructose (1 g), Na-formate (0.4 g), $NAD^+$ (0.005 g), calcium pyrophosphate (0.3 g), ascorbic acid (4 g=concentration per 100 kg), 0.005M acetate buffer pH 6.0 (37 ml[b]), MDH+fructose (100-500 U MDH[b]+1 g fructose), FDH+Na-formate (50 U FDH+0.4 g Na-formate). For the buffer and the MDH, the amount of water was corrected for the addition of buffer or MDH solution ([b]).

Compounds were tested alone or in combination. Effects e.g. are shown in FIGS. 2, 5 and 6.

Example 10

The MDH Regeneration System

The reaction mixture for the pre-fermentation period contained 10% (w/v) flour, 10% glucose solution and yeast (100*=100 times the yeast/flour ratio normally used in dough). This mixture was incubated during 20 minutes at 25° C. After this pre-fermentation period, $NAD^+$ was added in a concentration of 0.5 mM (=T0) (pre-incubation period). After another 30 minutes, glucose (10%), D-fructose (100 mM) and mannitol dehydrogenase (MDH) (activity as specified) were added to the reaction mixture (=T1). Most components were dissolved in an acetate buffer to reach a final pH of 5.5 and a buffer concentration of 0.1 M. When not specified, the MDH was from *L. pseudomesenteroides* ATCC 12291. For the blank, the MDH solution was replaced by a 0.05 M acetate buffer (pH 6), used to dissolve the MDH. For the addition of MDH at T0, $NAD^+$, glucose, fructose and MDH were all added at the same time, i.e. after the 20 minutes pre-fermentation period. MDH activity was measured spectrophotometrically. 50 μl of MDH enzyme extract was added to a reaction mixture containing 200 μl 10% glucose solution, 200 μl 1.25 mM NADH solution (prepared in a 0.125 mM acetate buffer at pH 5.5), 100 μl physiological solution and 50 μl 1.2 M D-fructose solution (also prepared in 0.2 M acetate buffer at pH 5.5). The absorbance change at 340 nm was recorded as a function of time. The initial linear decrease in absorbance was calculated ($\Delta A340$/min) and used to determine the enzyme activity as U per l reaction mixture.

$$U/l_{reaction\ mixture} = (\Delta A340\ nm/min) * (1000/6.22)$$

Example 11

In Vitro NPP Inhibition Studies

To perform in vitro nucleotide pyrophosphatase (NPP) inhibition studies, a reaction mixture of 5 ml was made containing 2.5 ml of flour extract (see Example 12), 1.5 ml of $NAD^+$ or NADH solution and 1 ml of potential inhibitor. The coenzymes and inhibitors were dissolved in a 0.2 M acetate buffer at pH 5.5. The final coenzyme concentration was 0.5 mM, unless otherwise mentioned. The final concentration of the different inhibitors tested is given in table 3. The different phosphates (disodium phosphate ($Na_2H_2P_2O_7$), sodium metaphosphate ((NaPO$_3$)$_n$), pentasodium tripolyphosphate (Na$_5$P$_3$O$_{10}$), tetrasodium pyrophosphate (Na$_4$P$_2$O$_7$) and dicalcium pyrophosphate (CaH$_2$P$_2$O$_7$)) were tested in a concentration of 10 g/l. For the reactivation experiments with metal ions and to test a synergetic effect of glycine with EDTA the reaction mixture was adapted: 500 µl of inhibitor was added together with 500 µl of cation or glycine instead of 1 ml inhibitor. For the reactivation experiments with metal ions, the chloride forms of the cations were used, i.e. MgCl$_2$, MnCl$_2$, ZnCl$_2$ and CaCl$_2$.

TABLE 3

Concentration of the potential inhibitors in the final reaction mixture

| Inhibitor | Concentration (mM) |
| --- | --- |
| EDTA | 0.003-10 |
| AMP | 0.5-10 |
| ADP | 1 |
| Nicotinamide | 10 |
| DTT | 4 |
| L-cysteine | 0.1-40 |
| Reduced glutathione | 10 |
| Mercaptoethanol | 16 |

TABLE 3-continued

Concentration of the potential inhibitors in the final reaction mixture

| Inhibitor | Concentration (mM) |
| --- | --- |
| Sodium pyrophosphate | 20-100 |
| Calcium pyrophosphate | 10-100 |
| Glycine | 5-100 |

Example 12

Preparation of a Wheat Flour Extract

A flour extract was prepared based on the method described by Honold et al. (1966, *Cereal Chemistry* 43:517-528). To 5 g of flour, 25 ml of an aqueous 12.5% sucrose solution was added. The solution was homogenised with an UltraTurrax mixer (IKA Werke, Janke & Kunkel GmbH & CoKG, Staufen, Germany). This homogenised flour suspension was centrifuged during 5 minutes at 1000 rpm (77 g) (SS34 rotor, Sorvall RC 5B centrifuge). The supernatant was recovered and filtrated through Whatman No. 1 filter paper. The filtrate was used as crude flour extract. All steps were carried out between 0° C. and 5° C.

The invention claimed is:

1. A method for inhibiting nicotinamide coenzyme degradation in a wheat based product, comprising adding an effective nicotinamide coenzyme degradation-inhibiting amount of nucleotide pyrophosphatase inhibitor and a coenzyme regeneration system to said wheat based product, wherein the coenzyme regeneration system comprises at least one NAD(P) or NAD(P)H dependent mannitol dehydrogenase and D-fructose.

2. The method of claim 1, wherein the nucleotide pyrophosphatase inhibitor is pyrophosphate.

3. The method of claim 1, wherein the wheat based product is a dough.

4. The method of claim 3 wherein the dough is yeast-raised.

5. The method of claim 1, wherein said nucleotide pyrophosphatase inhibitor inhibits a nucleotide pyrophosphatase present in the wheat based product and has an N-terminal amino acid sequence of SEQ ID NO: 1 or SEQ ID NO: 2.

6. The method of claim 1, wherein at least 70% inhibition of the nucleotide pyrophosphatase is obtained by the addition of the inhibitor.

7. The method of claim 2, wherein the wheat based product is a dough.

8. The method of claim 2, further comprising adding a coenzyme regeneration system to the wheat based product.

9. The method of claim 3, further comprising adding a coenzyme regeneration system to the wheat based product.

10. The method of claim 4, further comprising adding a coenzyme regeneration system to the wheat based product.

11. A dough comprising a nucleotide pyrophosphatase inhibitor and a coenzyme regeneration system comprising at least one NAD(P) or NAD(P)H dependent mannitol hydrogenase and D-fructose.

12. The dough of claim 11, wherein the nucleotide pyrophosphatase inhibitor is pyrophosphate.

13. A method for inhibiting nicotinamide coenzyme degradation in a wheat based product, comprising adding an effective nicotinamide coenzyme degradation-inhibiting amount of nucleotide pyrophosphatase inhibitor and a coenzyme regeneration system, wherein at least 70% inhibition of the nucleotide pyrophosphatase is obtained by the addition of the inhibitor.

* * * * *